United States Patent
Narishige et al.

(10) Patent No.: US 7,358,721 B2
(45) Date of Patent: Apr. 15, 2008

(54) EDDY CURRENT FLAW DETECTION SENSOR AND METHOD

(75) Inventors: Soshi Narishige, Hitachi (JP); Akira Nishimizu, Tokai (JP); Masahiro Koike, Hitachi (JP); Yoshiharu Abe, Hitachi (JP); Yuuichi Narumi, Hitachiohta (JP); Hirofumi Ouchi, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 11/680,857

(22) Filed: Mar. 1, 2007

(65) Prior Publication Data
US 2007/0229066 A1    Oct. 4, 2007

(30) Foreign Application Priority Data
Mar. 3, 2006    (JP) .............................. 2006-057841
Jan. 11, 2007    (JP) .............................. 2007-003694

(51) Int. Cl.
*G01N 27/82*    (2006.01)
*G01N 27/90*    (2006.01)
(52) U.S. Cl. ..................... 324/240; 324/242; 324/243

(58) Field of Classification Search ........ 324/219–221, 324/228, 237–243
See application file for complete search history.

(56) References Cited

U.S. PATENT DOCUMENTS
4,235,020 A * 11/1980 Davis et al. .................. 33/544
7,256,577 B2 * 8/2007 Linn et al. .................. 324/240

FOREIGN PATENT DOCUMENTS
JP    06-160357    6/1994
JP    3406649      3/2003
JP    2003-149210  5/2003

* cited by examiner

*Primary Examiner*—Bot LeDynh
(74) *Attorney, Agent, or Firm*—Mattingly, Stanger, Malur & Brundidge, P.C.

(57) ABSTRACT

An eddy current flaw detection sensor is provided which can detect a circumferential crack occurring at the deformed portion or peripheral portion thereof of a heat transfer tube with a high degree of sensitivity. Two excitation coils 1a, 1b cause eddy current B to flow in the axial direction of a tubular test object 31. A detection coil 2 disposed between the excitation coils 1a, 1b detects bypass eddy current D which flows in the circumferential direction of the test object 31 while bypassing a circumferential crack E. For this purpose, the coil axes of the excitation coils 1a, 1b are directed to the radial direction of the cylindrical protection member 3 and the coil axis of the detection coil 2 is directed to the axial direction of the protection member 3.

15 Claims, 18 Drawing Sheets

EDDY CURRENT FLAW DETECTION SENSOR AND METHOD

Under 35 USC 119, this application claims the benefit of foreign priority applications filed in Japan, serial number 2006-057841, filed Mar. 3, 2006, and serial number 2007-003694, filed Jan. 11, 2007, the disclosures of which are incorporated by reference herein.

BACKGROUND OF THE INVENTION

1. Field of the Invention

The present invention relates to an eddy current flaw detection sensor and method. In particular, the invention relates to arrangement of excitation and detection coils of an eddy current flow detection sensor in which the excitation coils are disposed on both sides of at least one detection coil and a method of detecting a circumferential crack occurring at a tubular test object by use of the sensor.

2. Description of the Related Art

The heat transfer tube of a heat exchanger installed in the cooling material purification system, etc. of an atomic power plant is subjected to periodic inspections to determine if a flaw such as a crack or the like occurs or not. An eddy current flaw detection method is usually adopted as a method of detecting a heat transfer tube of such a case, because this method exhibits high surface sensitivity, enables high-speed and noncontact flaw detection and additionally is appropriate for automatic flaw detection and remote control.

The eddy current flaw detection method is a nondestructive test method. In this method, alternating voltage is applied to an excitation coil provided for the eddy current flaw detection sensor to generate an eddy current in a planar direction of a test object made of a conductor while an eddy current flaw detection sensor scans the test surface. When an eddy current is caused to flow to a possible defective portion, a change of signal appearing in a detection coil is observed. Thus, the presence or absence, position, size and the like of a flaw is determined.

An eddy current flaw detection probe is proposed as the eddy current flaw detection sensor which has been applied to a tubular test object such as a heat transfer tube or the like. In the eddy current flaw detection prove shown in FIGS. 17A and 17B, two excitation coils 101, 102 reverse to each other in winding direction are arranged almost parallel to each other. Between the two excitation coils 101, 102, detection coils 103a to 103h having the same winding direction are disposed almost parallel to the axial direction of the excitation coils 101, 102 and radially around the axis thereof. See JP-A-2003-149210, [0013] to [0016].

This eddy current flaw detection probe performs flaw detection from the inner surface of the tubular test object A by being inserted into the test object A. More specifically, excitation current is applied to the excitation coils 101, 102 while the eddy current flaw detection probe is inserted in the tubular test object A. At that time, eddy currents flowing in the circumferential direction of the test object A are superposed on the wall surface of the test object A facing the intermediate area between the two excitation coils 101, 102. As shown in FIG. 17B, an eddy current distribution B is formed around the detection coils 103a to 103h so as to reach the deep layer portion of the test object A. Accordingly, the position, shape, sized and the like of a flaw C can be detected by the detection coils 103a to 103h detecting bypass eddy current D which flows in the axial direction X-X of the test object A while bypassing the flaw C extending parallel to the axial direction X-X of the test object A as shown in FIG. 18.

An eddy current probe described below has been proposed as the eddy current flaw detection sensor of this type. As shown in FIGS. 19A and 19B, this eddy current probe includes a columnar-formed probe main body 200 and two coil units arranged in the axial direction of the main body 200. Each of the coil units has a combination of a plurality of eddy current generation coils 201 and of detection coils 202. The eddy current generation coils 201 and the detection coils 202 constituting one of the coil units are arranged to be offset from those of the other coil unit in the circumferential direction of the probe main body 200. See JP No. 3406649, [0019] to [0023]. This patent document also discloses a technique of connecting in series the plurality of eddy current generation coils 201 constituting each coil unit.

The eddy current flaw detection sensor described above can detect a flaw occurring in the axial and circumferential directions of a tube.

SUMMARY OF THE INVENTION

Incidentally, the heat transfer tube of the heat exchanger is formed in a U-shape and is fastened to a magnetic member called a tube sheet in such manner that both ends thereof are inserted into heat transfer tube through-holes bored in the tube sheet. The method of fastening the heat transfer tube to the tube sheet adopts a tube expansion method which expands the diameter of the heat transfer tube inserted into the heat transfer tube through holes from the inside thereof, thereby bringing the tube sheet and the external surface of the heat transfer tube into close contact. FIG. 20 is a cross-sectional view of an essential part of a tube sheet and a heat transfer tube fastened thereto. In the figure, reference numeral 111 denotes a tube sheet, 112 denotes a heat transfer tube through-hole disposed at the tube sheet 111, 113 denotes a heat transfer tube, 114 denotes an tube expansion portion of the heat transfer tube 113, and 115 denotes a deformed portion formed at the boundary portion between the tube expansion portion 114 and a tube non-expanded portion. As obvious from the figure, the tube expansion portion 114 is formed within the range of the thickness of the tube sheet 111 and the deformed portion 115 is formed almost uniformly over the entire circumference of the heat transfer tube 113.

The heat transfer tube 113 is continuously subjected to stress resulting from the operation of the heat exchanger. The heat transfer tube 113 is locally fastened to the tube sheet 111 at both the ends thereof. Therefore, the stress concentrates on the deformed portion 115. Thus, as shown in FIG. 20, a circumferential crack E extending along the deformed portion 115 and in the circumferential direction of the heat transfer tube 113 is liable to occur.

Accordingly, to perform maintenance of the heat transfer tube 113, it is necessary to detect the presence or absence of such a circumferential crack E with a high degree of sensitivity. Like the eddy current flaw detection probe described in JP-A-2003-149210, it is difficult for the eddy current flaw detection sensor, which allows the eddy current B to flow in the circumferential direction Y-Y of the tubular test object A, to detect the circumferential crack E of the heat transfer tube 113 with a high degree of sensitivity.

More specifically, the eddy current flaw detection probe described in JP-A-2003-149210 allows the eddy current B to flow in the circumferential direction Y-Y of the heat transfer tube 113. Therefore, as shown in FIG. 21, the bypass eddy current D which flows in the axial direction X-X of the heat transfer tube 113 while bypassing the circumferential crack E is minute as compared with the axial crack. On the other hand, for the tube expansion portion 114 of the heat transfer tube, the change in the shape of the heat transfer tube 113 and the change in the eddy current distribution resulting from the presence or absence of the tube sheet 111 become noise. The noise is significantly greater than the magnitude of a signal obtained by detecting the bypass eddy current D. Thus, the eddy current flaw detection probe described in JP-A-2003-149210 cannot detect the circumferential crack E with a high degree of sensitivity.

The eddy current flaw detection probe described in JP No. 3406649 is configured to be able to detect both flaws occurring in the axial and circumferential directions of the tube. Therefore, it is impossible to differentiate the change in the shape of the heat transfer tube 113 in the deformed portion 115 and the change in the eddy current distribution resulting from the presence or absence of the tube sheet 111 in the tube expansion portion 114 from the bypass eddy current D occurring along the circumferential crack E of the heat transfer tube 113. That is to say, the circumferential crack E of the heat transfer tube 113 cannot be detected with a high degree of sensitivity.

The present invention has been made to solve the disadvantage of such a conventional art and it is an object of the invention to provide an eddy current flaw detection sensor which can detect a circumferential crack occurring at the deformed portion or peripheral portion thereof of a heat transfer tube with a high degree of sensitivity.

The object is achieved by using an eddy current flaw detection sensor including excitation coils allowing eddy current to flow in the axial direction of a tubular test object and a detection coil detecting a bypass eddy current flowing in the circumferential direction of the test object.

According to one aspect of the present invention, there is provided an eddy current flaw detection sensor which includes at least one detection coil, and excitation coils disposed on both sides of the detection coil, wherein a coil axis of the detection coil and coil axes of the excitation coils are arranged to intersect each other, and when the detection coil and the excitation coils are inserted into a tubular test object and excitation current is applied to the excitation coils, eddy current flows in the axial direction of the tubular test object and the detection coil can detect eddy current flowing the circumferential direction of the tubular test body.

With such a configuration, application of excitation voltage to the excitation coils causes eddy current to flow in the axial direction of a tubular test object and the detection coil can detect bypass eddy current which flows in the circumferential direction of the tubular test object while bypassing a circumferential crack. In this way, allowing the eddy current to flow in the axial direction of the tubular test object can make the direction of the circumferential crack occurring in the tubular test object orthogonal to the flowing direction of the eddy current flowing in the tubular test object. Therefore, the flow rate of the bypass eddy current which flows in the circumferential direction of the tubular test object while bypassing the circumferential crack can be increased as compared with the case where the eddy current is allowed to flow in the circumferential direction of the tubular test object. Since being present on the entire circumference of the tubular test object, changes in the shape of the tubular test object and the tube sheet made of a magnetic material are unlikely to generate the bypass eddy current. Even if the eddy current flowing in the circumferential direction is generated, since the bypass eddy current flowing clockwise and counterclockwise is generated around the tubular test object, the eddy current and the bypass eddy current cancel each other when detected, thereby suppressing noise. This increases the signal-to-noise ratio of the detected signal, whereby the presence or absence, occurrence position, size and the like of a circumferential crack of the tubular test object can be detected with a high degree of accuracy.

Preferably, in the first eddy current flaw detection sensor described above, a plurality of the excitation coils are evenly arranged in the circumferential direction of a retaining member and a single of or a plurality of the detection coils are evenly arranged between the excitation coils. With such a configuration, the eddy current can be allowed to flow over the entire circumference of the tubular test object. Therefore, it is eliminated to operatively rotate the eddy current flaw detection sensor around the central axis of the tubular test object, thereby significantly streamlining the flaw detection of the tubular test object.

Preferably, in the second eddy current flaw detection sensor described above, two of the detection coils reverse to each other in winding direction are disposed between the excitation coils so as to be juxtaposed in an axial or circumferential direction of a retaining member. With such a configuration, the winding directions of the two detection coils disposed between the two excitation coils are reverse to each other. Therefore, signals can be detected which correspond to the positive and negative directions of bypass eddy currents which flow in the circumferential direction of the tubular test object while bypassing the circumferential crack. Thus, the detection level of the signal is increased, whereby the occurrence position and size of the circumferential crack can be precisely detected.

Preferably, in the second eddy current flaw detection sensor described above, four of the detection coils reverse to each other in winding direction are disposed between the excitation coils so as to be arranged in the axial and circumferential directions of the retaining member in an matrix manner. With such a configuration, the four detection coils arranged in the two excitation coils are reverse to each other in winding direction. Therefore, the signals which correspond to the positive and negative directions of bypass eddy currents flowing in the circumferential direction of the tubular test object while bypassing the circumferential crack can be detected. Thus, the detection level of the signal is increased, whereby the occurrence position and size of the circumferential crack can be further precisely detected.

Preferably, in the first to forth eddy current flaw detection sensor described above uses a winding wire of the excitation coil has a planar shape formed in an oval. Such a configuration can cause greater eddy current to flow in the test object than the case of using the excitation coil having a winding shape formed in a column if the excitation coils have the same number of windings. Thus, the circumferential crack can be detected with a high degree of accuracy.

Preferably, in the second eddy current flaw detection sensor described above uses the retaining member which has an outer shape formed in a column. Thus, this detection sensor can be a practical eddy current flaw detection sensor for tube-inspection, which is insertable into a tubular test object.

Preferably, in the second eddy current flaw detection sensor includes a plurality of sensor units arranged in an axial direction of the retaining member, each sensor unit including a plurality of excitation coils and a single of or a plurality of detection coils disposed between the excitation coils arranged in the circumferential direction of the retaining member. In addition, the excitation coils and the detection coils constituting one of the sensor units are arranged to be offset from those constituting another of the sensor units in the circumferential direction of the retaining member. It is assumed that the center of the detection coil is located at a position where positive and negative bypass eddy currents which flow in the circumferential direction of the tubular test object while bypassing a circumferential crack are equal to each other. In this case, a structure provided with a single sensor unit produces a dead zone where the bypass eddy current cannot be detected. In contrast to this structure, the plurality of sensor units is arranged in the axial direction of the retaining member and the excitation coils and the detection coils constituting one of the sensor units are arranged to be offset from those of the other sensor unit. Even if a dead zone occurs for the detection coil provided for one sensor unit, the detection coil provided for the other sensor unit can reliably detect a circumferential crack of a tubular test object. Thus, reliability of eddy current detection can be enhanced.

Preferably, in the seventh eddy current flaw detection sensor described above, the plurality of excitation coils constituting the sensor units are connected in series or parallel in such a manner that the winding directions of adjacent excitation coils disposed in the circumferential direction of the retaining member via the detection coil are reversed to each other, and both ends of the plurality of excitation coils connected in series or parallel are connected to one excitation power source. With this configuration, wiring used to connect the plurality of excitation coils with the excitation power source can be shared by the excitation coils; therefore, the wiring space for the eddy current flaw detection sensor can be reduced. Since the excitation voltages with the same waveform can be applied to the plurality of excitation coils at the same time, a single application of the excitation voltage can cause eddy current to flow on the entire circumference of the tubular test body. This can enhance inspection efficiency for the tubular test object. In addition, the plurality of excitation coils constituting the sensor units are connected in series or parallel in such a manner that the winding directions of the adjacent excitation coils disposed in the circumferential direction of the retaining member through the detection coil are reversed to each other. Thus, the eddy currents under the detection coils form a distribution where their directions are reversed to each other. The eddy currents flowing under the detection coils interfere with each other so as to increase with each other, thereby enhancing the signal-to-noise ratio of a detected signal.

According to another aspect of the present invention, there is provided an eddy current flaw detection method which detects a flaw of a tubular test object by inserting, into the test object, an eddy current flaw detection sensor provided with excitation coils and a detection coil. In this method, the eddy current flaw detection sensor includes at least one detection coil and excitation coils disposed on both sides of the detection coil, a coil axis of the detection coil and coil axes of the excitation coils are arranged to intersect each other, and when the detection coil and the excitation coils are inserted into a tubular test object and excitation voltage is applied to the excitation coils, eddy current flows in the axial direction of the tubular test object and the detection coil can detect eddy current flowing in the circumferential direction of the test object.

In the eddy current flaw detection method which detects a flaw of a tubular test object by inserting the eddy current flaw detection sensor into the test object, the eddy current flaw detection sensor configured described above is used to apply excitation voltage to the excitation coils described above. This application causes eddy current to flow in the axial direction of the tubular test object and bypass eddy current to flow in the circumferential direction of the tubular test object while bypassing the circumferential crack. This bypass eddy current can be detected by the detection coil. Thus, the signal-to-noise ratio of the detected signal can be enhanced, and the presence or absence, position of occurrence, size and the like of the circumferential crack in the tubular test object can be detected with a high degree of reliability.

Preferably, in the first eddy current flaw detection method described above, the eddy current flaw detection sensor used is configured such that a plurality of the excitation coils are evenly arranged in the circumferential direction of a retaining member, a single of or a plurality of the detection coils are evenly arranged between the excitation coils and the plurality of excitation coils are connected in series or parallel. In addition, excitation voltage with the same waveform is applied to the plurality of excitation coils connected in series or parallel at the same time, thereby causing eddy currents reverse to each other in direction to flow under the detection coils adjacent to each other from the excitation coils arranged in the circumferential direction of the retaining member via the detection coil. Thus, since the eddy current can be caused to flow on the entire circumference of the tubular test object, the one cross-section of the tubular test body can be inspected at one time, which makes it possible to enhance the inspection efficiency for the tubular test object.

Preferably, in the eddy current flaw detection method described above, the tubular test object is a tube expansion portion of a heat transfer tube of a heat exchanger provided for an atomic power plant. Thus, the tube expansion portion of heat transfer tube of the heat exchanger which tends to cause a circumferential crack can be inspected easily and reliably.

The eddy current flaw detection sensor of the present invention includes the excitation coils which cause eddy current to flow in the axial direction of the tubular test object and the detection coil which detects bypass eddy current flowing in the circumferential direction of the test object. Therefore, a circumferential crack occurring at the deformed portion or peripheral portions thereof of the heat transfer tube can be detected with a high degree of sensitivity.

The eddy current flaw detection method of the present invention causes the detection coil to detect bypass eddy current flowing in the circumferential direction of the tubular test object while applying excitation voltage to the excitation coils to cause eddy current to flow in the axial direction of the tubular test object. Therefore, the circumferential crack occurring at the deformed portion or peripheral portions thereof of the heat transfer tube can be detected with a high degree of sensitivity.

DETAILED DESCRIPTION OF THE PREFERRED EMBODIMENTS (Eddy Current Flaw Detection System)

Figure 1:
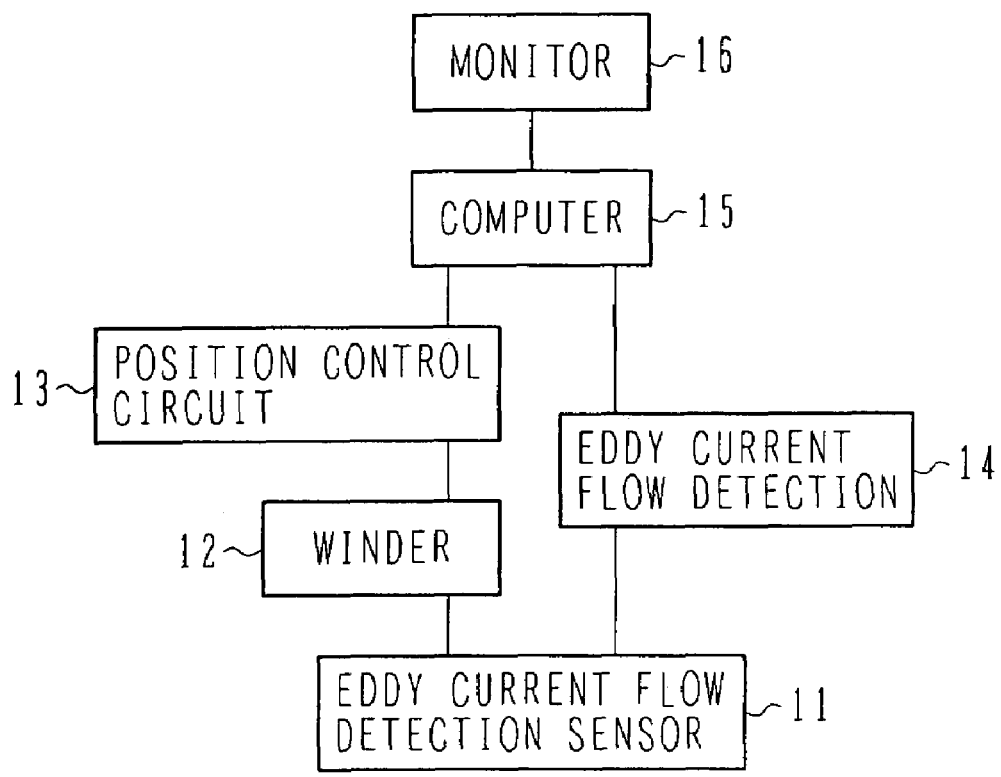
FIG. 1 is a block diagram illustrating the configuration of an eddy current flaw detection system.

Before the explanation of an eddy current flaw detection sensor according to the present invention, a configuration of an eddy current flaw detection system using the detection sensor is described with reference to FIGS. 1 and 2. FIG. 1 is a block diagram of the eddy current flaw detection system and FIG. 2 is a block diagram of the eddy current flaw detector.

As shown in FIG. 1, the eddy current flaw detection system of the embodiment includes an eddy current flaw detection sensor 11, a winder 12 for a lead wire connected to the detection sensor 11 and a position control circuit 13 which controls an amount of feeding the lead wire from the winder 12. In addition, the eddy current flaw detection system includes an eddy current flaw detector 14, a computer 15 and a monitor 16. The eddy current flaw detector 14 supplies excitation current to the eddy current detection flaw sensor 11 and detects an induced voltage signal from the detection sensor 11. The computer 15 controls drive of the winder 12 through the position control circuit 13 and drive of the detection sensor 11 via the eddy current detector 14. The monitor 16 displays the operation states of the above components, the induced voltage signal detected by the detection sensor 11 and so forth. The winder 12, the position control circuit 13, the eddy current detector 14, the computer 15 and the monitor 16 can use commercialized products.

Figure 2:
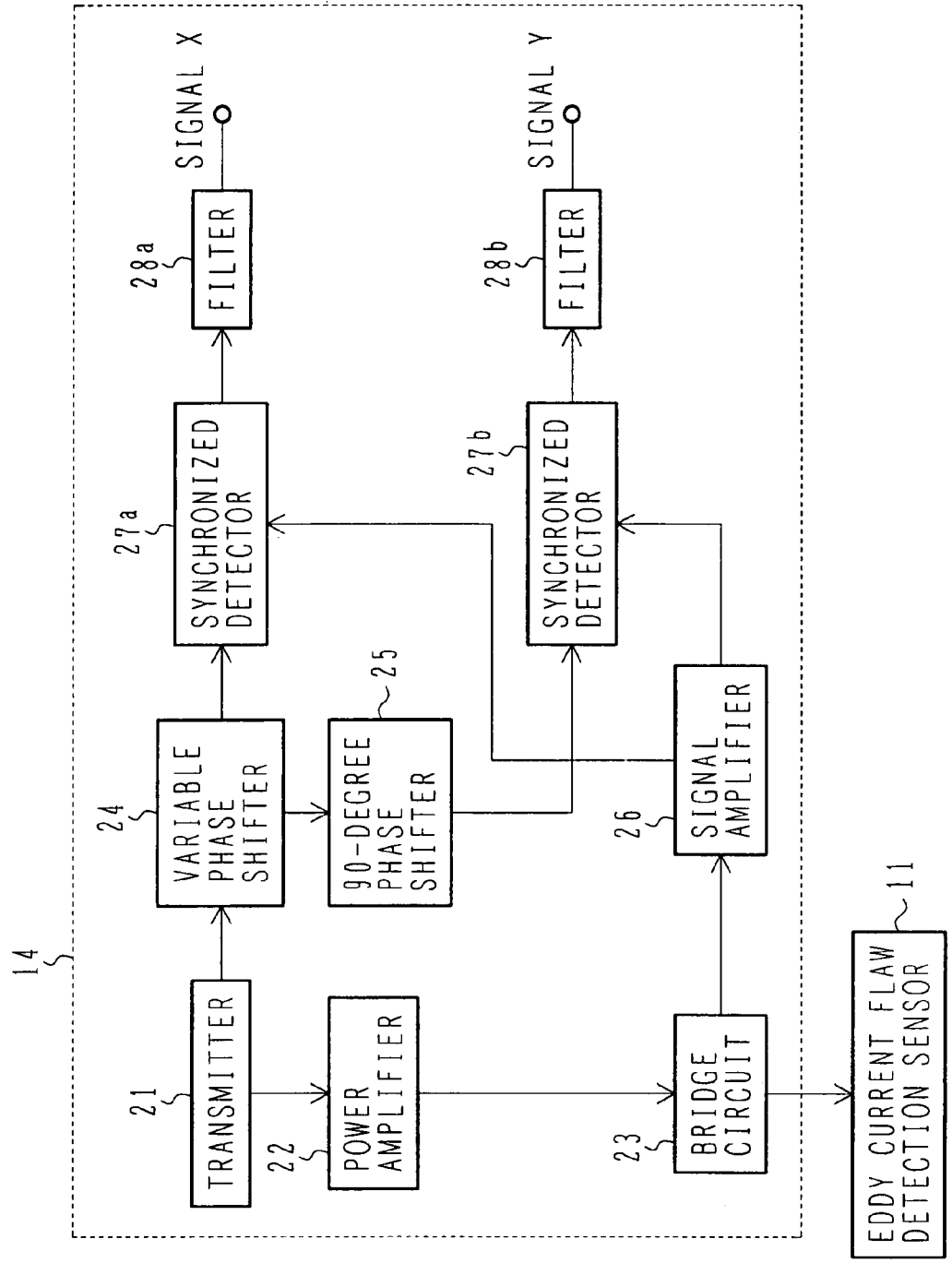
FIG. 2 is a block diagram of an eddy current flaw detector.

Referring to FIG. 2, the eddy current detector 14 includes a transmitter 21, a power amplifier 22, a bridge circuit 23, a variable phase shifter 24, a 90-degree phase shifter 25, a signal amplifier 26, two synchronized detectors 27a, 27b, and two filters 28a, 28b. The transmitter 21 applies alternating voltage with a frequency f (f is 1 KHz to 1 MHz) to excitation coils provided for the eddy current flaw detection sensor 11 through the power amplifier 22. The bridge circuit 23 which includes as a constituent element a detection coil provided for the eddy current flaw detection sensor 11 produces voltage resulting from imbalance of impedance across the terminals of the bridge circuit. The signal amplifier 26 amplifies the voltage and sends the amplified voltage to the two synchronized detectors 27a, 27b. One synchronized detector 27a synchronously detects as a reference waveform alternating voltage, from the transmitter 21, whose shift phase is arbitrarily adjusted by the variable phase shifter 24 and obtains a signal X via the filter 28a based on the output of the synchronous detection. The other synchronized detector 27b synchronously detects as a reference waveform alternating voltage via the 90-degree phase shifter 25 and obtains a signal Y via the filter 28b based on the output of the synchronous detection. It should be noted that this description intends to schematically explain the operation of the eddy current flaw detector 14. When the actual eddy current flaw detection is executed, the eddy current flaw detection sensor 11 according to the present invention is connected the input and output terminals of a commercially available eddy current flaw detector and signals X, Y are obtained from the waveform output terminal of the eddy current flaw detector.

The eddy current flaw detection system of the present embodiment exercises the whole control while the monitor 16 monitors the conditions and the computer 15 changes settings. The setting information (the drive-amount and drive-speed of the winder 12) of the computer 15 is sent to the position control circuit 13, and based on the information, electric power is fed from the position control circuit 13 to the winder 12. Thus, the amount of feeding the lead wire from the winder 12 is controlled. The setting information (transmitting frequency, voltage and so on) is sent to the eddy current flaw detector 14, and based on the information, alternating voltage with the setting frequency is applied from the eddy current flaw detector 14 to an external input terminal, on the excitation coil side, of the eddy current flaw detection sensor 11. The signal voltage from the external output terminal, on the detection coil side, of the eddy current flaw sensor 11 is sent to the eddy current flaw detector 14. The desired signal processing described above is executed in the eddy current flaw detector 14 and the output signal is sent to the computer 15 as a digital signal. The signal thus sent is observed by the monitor 16. These control proceeds temporally in parallel with each other and respective signals at shifted positions are monitored.

Embodiments of the eddy current flaw detection sensor 11 according to the present invention will be described below.

First Embodiment of the Eddy Current Flaw Detection Sensor

Figure 3A:
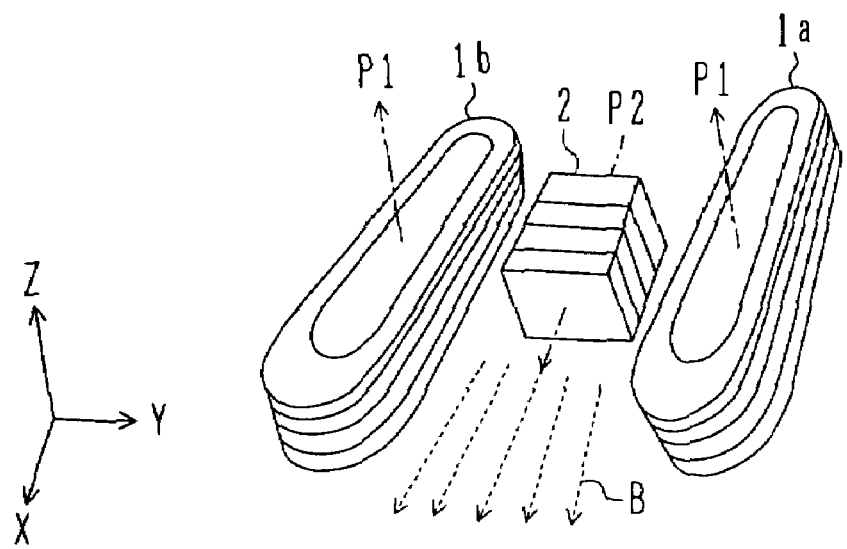
FIGS. 3A and 3B are views for assistance in explaining an eddy current flaw detection sensor according to a first embodiment.
Figure 3B:
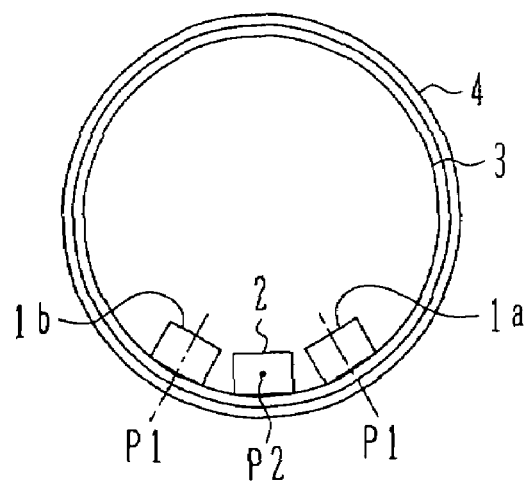
Figure 4:
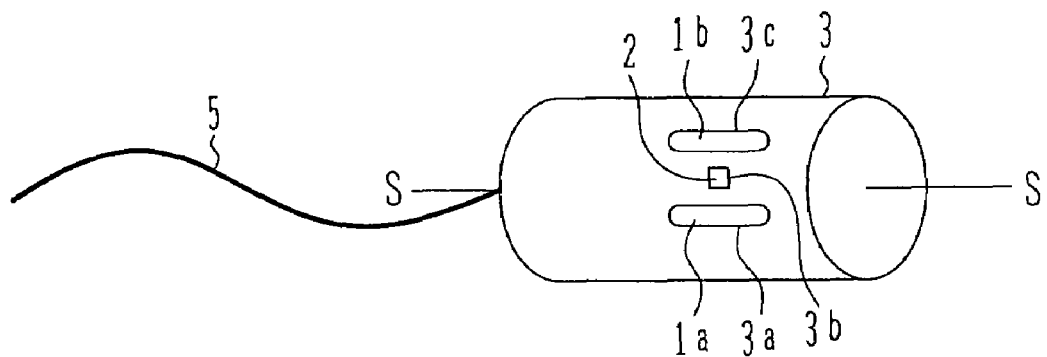
FIG. 4 is a perspective view of an eddy current flaw detection sensor according to the first embodiment.

Referring to FIGS. 3A, 3B and 4, an eddy current flaw detection sensor 11A according to a first embodiment includes two excitation coils 1a, 1b; one detection coil 2 disposed between the excitation coils 1a, 1b; a circular retaining member 3 integrally retaining the coils 1a, 1b, 2; a sheet-like protection cover 4 covering the surface of the retaining member 3; and multiple lead lines 5 connected to the corresponding coils 1a, 1b, 2.

The excitation coils 1a, 1b are each wounded in an oval including two circular arc portions and two straight portions connecting the two circular arc portions. The conductive wire has a diameter of 0.05 mm, the number of winding is 200, the circular arc portion has a curvature radius of 1 mm, and the straight portion has a length of 4 mm. A magnetic core made of ferrite or the like is integrally inserted into each of the excitation coils 1a, 1b. The two excitation coils 1a, 1b are formed to have the same shape and size.

In contrast, the detection coil 2 is wound in a rectangle or cylinder. The conductive wire has a diameter of 0.03 mm and the number of winding is 400. A magnetic core made of ferrite or the like is also integrally inserted into the detection coil 2.

The retaining member 3 is formed of an insulating material such as a polyacetal resin so as to be in a column having such a diameter that it is insertable into a tubular body such as a heat transfer tube which is a test object. The retaining member 3 is formed, on its surface in a circumferential direction, with respective recessed portions 3a, 3b, 3c conforming to the shapes of the excitation coil 1a, 1b and the detection coil 2 for burying the coils therein. The respective recessed portions 3a, 3c receiving the excitation coils 1a, 1b therein are formed to have a center-to-center distance of 8 mm so that their straight portions are opposed to each other.

As shown in FIGS. 3B and 4, the excitation coils 1a and 1b are respectively received in the elongate recessed portions 3a and 3c formed in the retaining member 3 so that their coil axes P1 are directed in the radial direction of the retaining member 3. The detection coil 2 is received in the rectangle hole-like recessed portion 3b formed in the retaining member 3 so that its coil axis P2 is directed in the direction of the center axis S of the retaining member 3. It should be noted that in the present specification "coil axis" means the winding center of a lead wire. To stabilize a coil axis, the coils 1a, 1b and 2 may be fixed in the respective recessed portions 3a, 3b and 3c by using a potting resin or the like. Each of the coils 1a, 1b, and 2 are directly connected at both ends thereof to lead lines 5 and are electrically connected to the input and output terminals of the eddy current flaw detector 14 via the lead lines 5. In this case, the two excitation coils 1a, 1b and the input and output terminals of the eddy current flaw detector 14 are connected to each other so that reverse excitation currents are applied to the excitation coils 1a, 1b. Thus, when the eddy current flaw detection sensor 11A of the present embodiment is inserted in the tubular test object and excitation voltage is applied to the excitation coils 1a, 1b, the distribution of eddy current that flows between the two excitation coils and in the axial direction of the test body and reaches the deep layer portion of the test object can be formed. On the other hand, the coil axis P2 of the detection coil 2 is directed to a direction parallel to the central axis S of the retaining member 3. Therefore, the detection coil 2 can detect the bypass eddy current flowing in the circumferential direction of the test object.

The protection cover 4 is adapted to protect the excitation coils 1a, 1b and the detection coil 2 from mechanical and chemical effects, and is formed of an insulative resin sheet or the like.

The lead line 5 is wound around the winder 12 and has one end connected to the eddy current flaw detector 14. Incidentally, it is desirable that the lead line 5 be provided with some kind of reinforcing means in order to alleviate damage resulting from abrasion occurring between the winder 12 and the lead line 5.

A description is below made of an experimental example using the eddy current flaw detection sensor 11A of the first embodiment configured as above and the eddy current flaw detection system described above.

A simulated test object of a heat transfer tube, namely, a simulated heat transfer tube 31 was prepared which had an outer diameter of 15.9 mm, a thickness of 2.3 mm and a material of SUS316. One end of the simulated heat transfer tube 31 was fastened to a simulated tube sheet 32 made of a magnetic material. The simulated heat transfer tube 31 was formed with a tube expansion portion 33, whose outer surface is fastened to a simulated heat transfer tube throughhole 34 bored in the simulated tube sheet 32. The step of a deformed portion 35 formed between the tube expansion portion 32 and the tube-non-expanded portion was about 0.1 mm in height on the inner surface of the simulated heat transfer tube 31. A crack E which extended in the circumferential direction of the simulated heat transfer tube 31 and had a depth of 0.46 mm on the outer surface thereof was formed at a position, of the outer surface of the simulated heat transfer tube 31, corresponding to the deformed portion 35. In addition, a simulated heat transfer tube 31 not formed with the circumferential crack E was prepared as a simulated test object of a heat transfer tube by way of comparative example. The other specifications of the other portions were the same as those of the simulated heat transfer tube 31 formed with the circumferential crack E.

Figure 5:
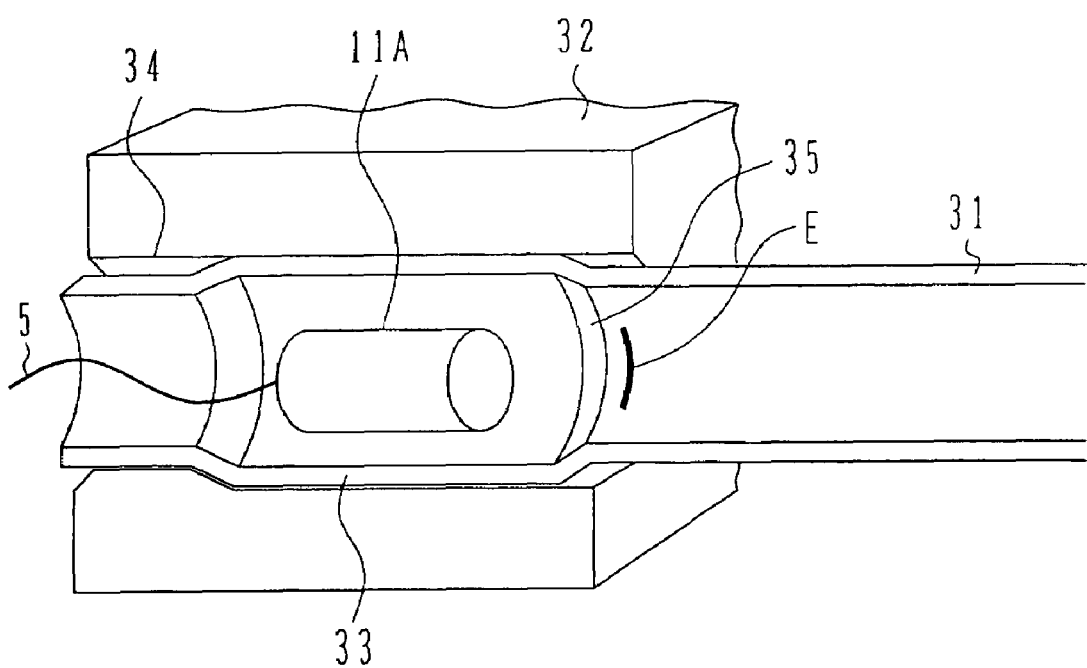
FIG. 5 is a cross-sectional view of an essential portion illustrating the configuration of a simulated test object and an eddy current flaw detection method.
Figure 10A:
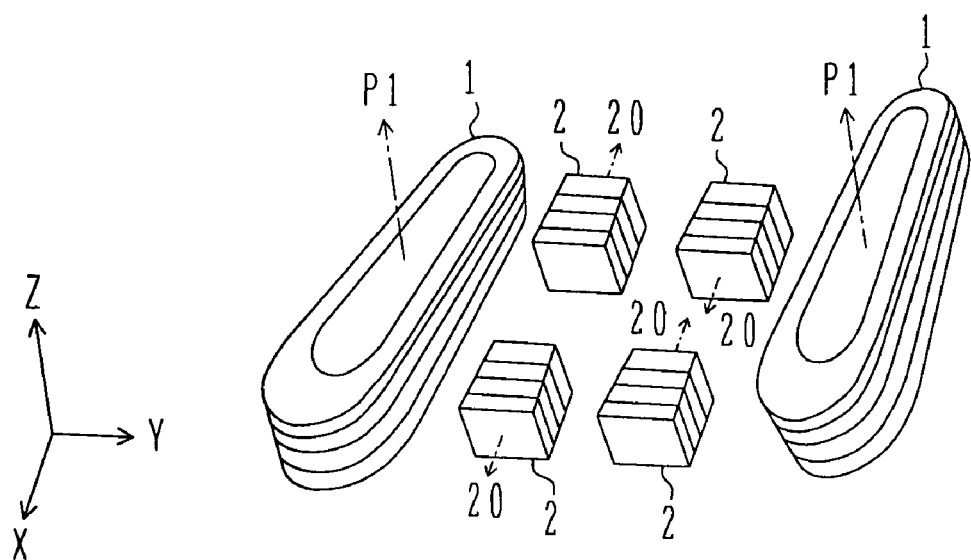
FIGS. 10A and 10B are views for assistance in explaining an eddy current flaw detection sensor according to a fourth embodiment.
Figure 10B:
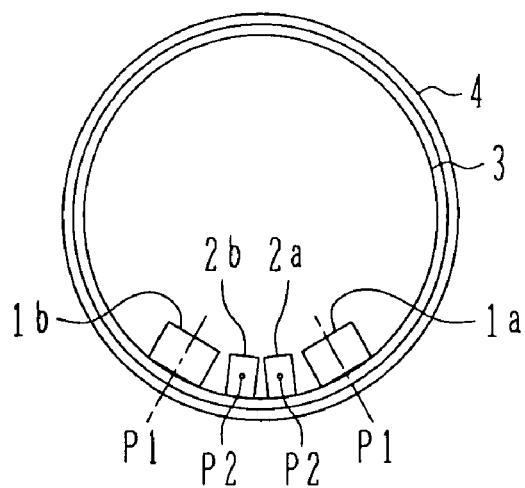

As shown in FIG. 5, the eddy current flaw detection sensor 11A of the first embodiment is inserted into the simulated heat transfer tube 31 from the opening end thereof. Then, the eddy current flaw detection was performed on the simulated heat transfer tube 31 by appropriately changing the settings of the computer 15 while monitoring the conditions with the monitor 16. In addition, the eddy current flaw detection probe simulating the conventional one shown in FIG. 10 is inserted into a simulated heat transfer tube 31 and then the eddy current flaw detection was performed on the simulated heat transfer tube 31 by the same method.

Figure 6:
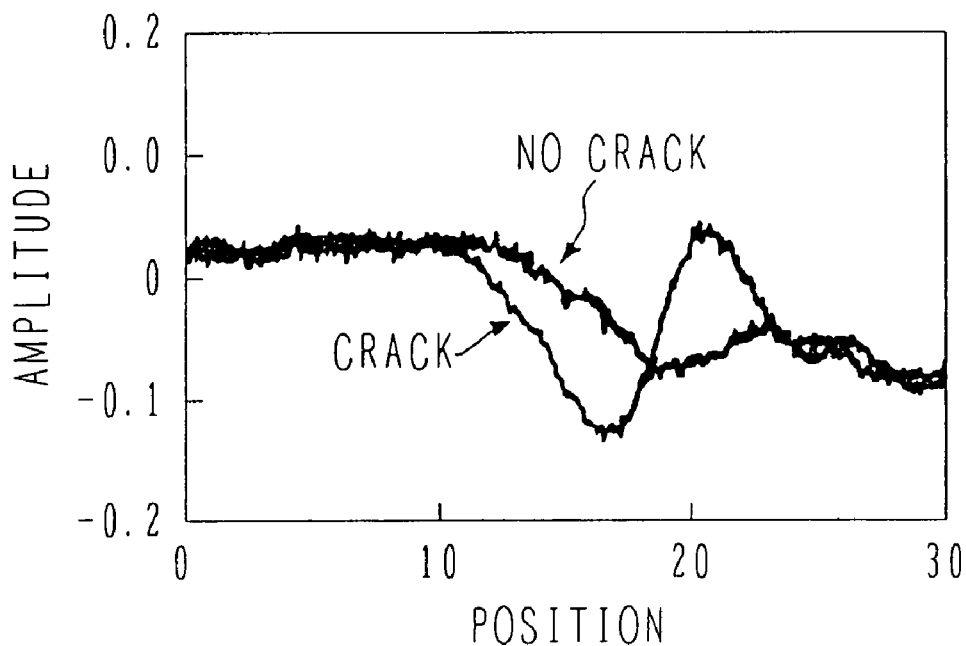
FIG. 6 is a waveform diagram of signals detected by the eddy current flaw detection sensor according to the first embodiment.
Figure 7:
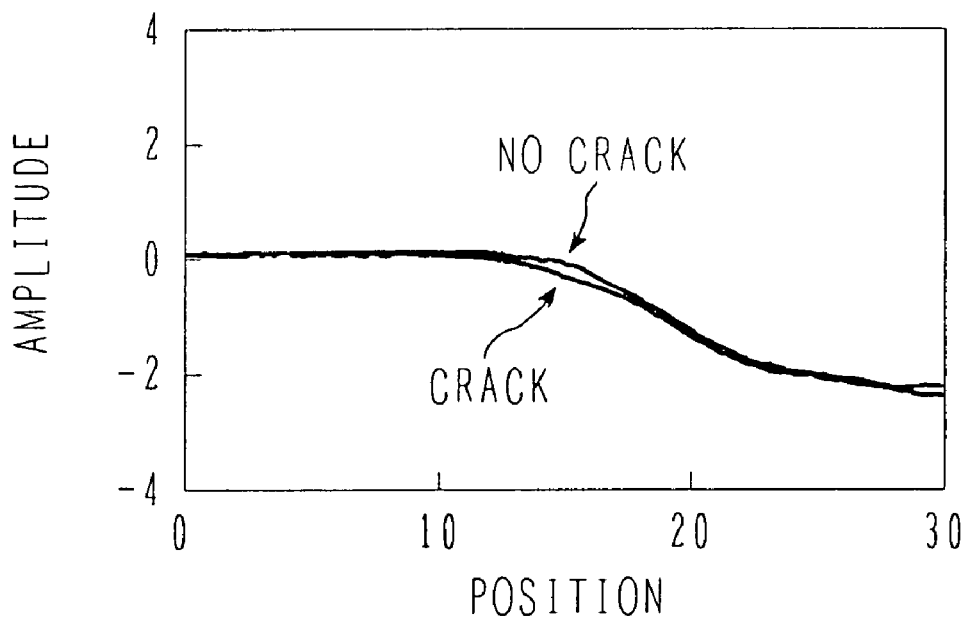
FIG. 7 is a waveform diagram of signals detected by a conventional type eddy current flaw detection sensor.

FIG. 6 illustrates waveforms of signals outputted from the detection coil 2 when the eddy current flaw detection of the simulated heat transfer tubes 31 is performed by using the eddy current flaw detection sensor 11A of the first embodiment. FIG. 7 illustrates waveforms of signals outputted from the detection coil when the eddy current flaw detection of the simulated heat transfer tube 31 was performed by using the conventional type eddy current flaw detection probe. When the conventional type eddy current flaw detection probe is used, as shown in FIG. 7, the signal waveform detected from the simulated test object which is the simulated heat transfer tube 31 not formed with the circumferential crack E is little different from that formed with the circumferential crack E. Consequently, the presence or absence of the circumferential crack E cannot be detected from the simulated test object. In contrast to this, when the eddy current flaw detection sensor 11A of the first embodiment is used, the signal waveform detected from the simulated test object which is the simulated heat transfer tube 31 not formed with the circumferential crack E is significantly different from that formed with the circumferential crack E. Consequently, the presence or absence, position, size of the circumferential crack E formed in simulated heat transfer tube 31 can be easily detected.

Second Embodiment of the Eddy Current Flaw Detection Sensor

Figure 8A:
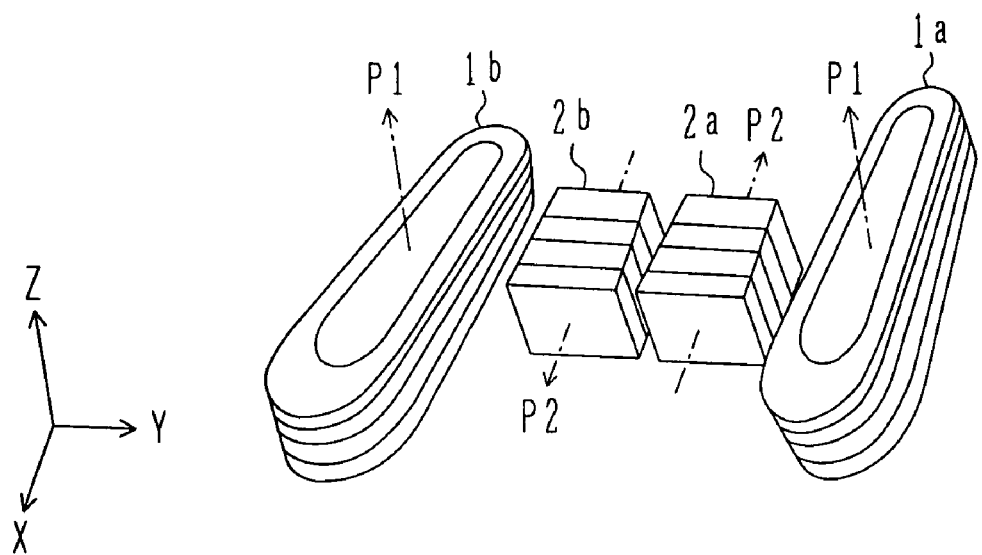
FIGS. 8A and 8B are views for assistance in explaining an eddy current flaw detection sensor according to a second embodiment.
Figure 8B:
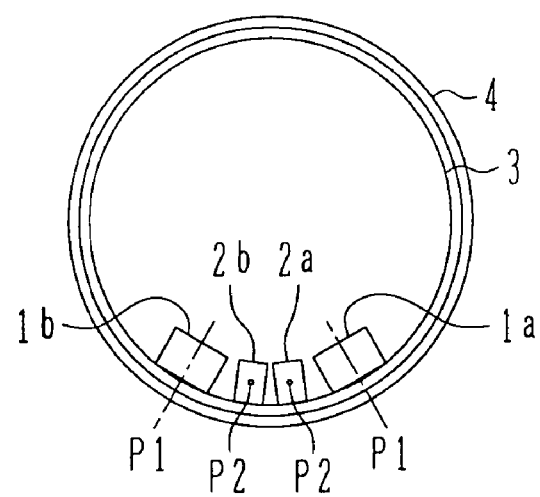

Referring to FIG. 8, an eddy current flaw detection sensor 11B according to a second embodiment is characterized in that two detection coils 2a, 2b different from each other in winding direction are disposed in the arranging direction of and between two excitation coils 1a and 1b. The two detection coils 2a, 2b are disposed at a lengthwise intermediate position between the excitation coils 1a, 1b so as to be evenly arranged in the circumferential direction of the retaining member 3. The other portions are the same as those in the eddy current flaw detection sensor 11A according to the first embodiment. Therefore, like or corresponding portions are denoted with like reference numerals and the duplicated explanations are omitted.

The eddy current flaw detection sensor 11B of the present embodiment includes the two detection coils 2a, 2b different from each other in winding direction disposed between the two excitation coils 1a, 1b. Signals can be detected which correspond to the positive and negative directions of bypass eddy currents D which flow in the circumferential direction of the heat transfer tube while bypassing the circumferential crack E. Thus, the detection level of the signal is increased compared with the case of one detection coil, whereby the detection sensitivity of the circumferential crack E is enhanced and the occurrence position and size thereof can be precisely detected.

Third embodiment of the Eddy Current Flaw Detection Sensor

Figure 9A:
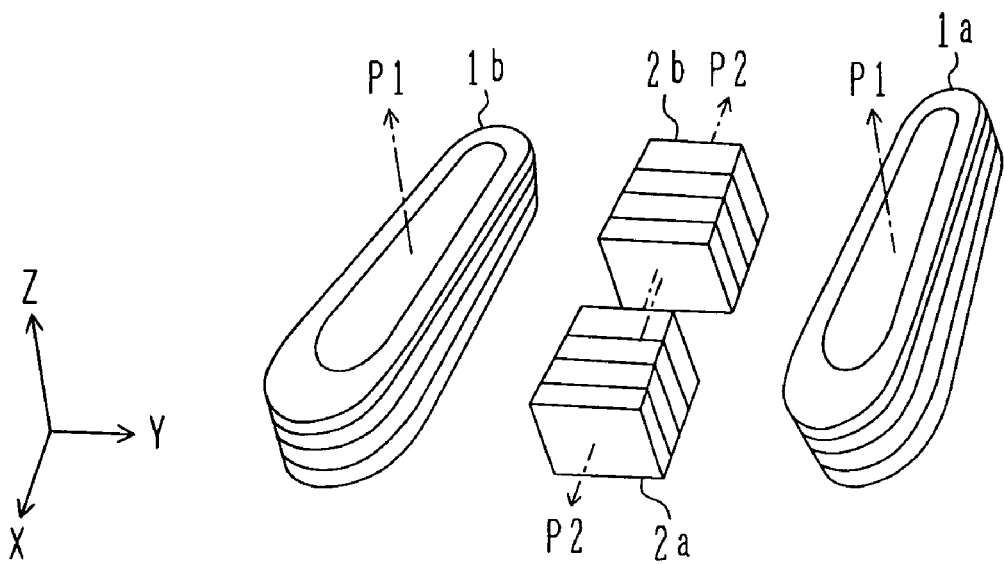
FIGS. 9A and 9B are views for assistance in explaining an eddy current flaw detection sensor according to a third embodiment.
Figure 9B:
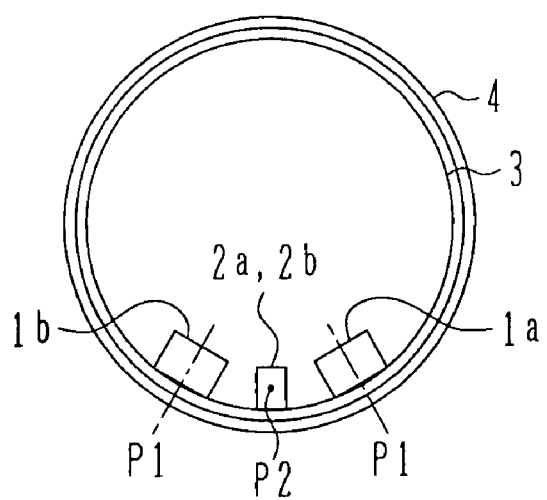

Referring to FIGS. 9A and 9B, an eddy current flaw detection sensor 11C according to a third embodiment is characterized in that two detection coils 2a, 2b different from each other in winding direction are disposed between two excitation coils 1a, 1b and in a direction crossing the arranging direction of the two excitation coils 1a, 1b. Specifically, the two detection coils 2a, 2b are disposed at a position evenly partitioning the two excitation coils 1a, 1b so as to be arranged in the axial direction of the retaining member 3. The axial distance between the respective centers of the two detection coils 2a, 2b is set to 6 mm. The other portions are the same as those in the eddy current flaw detection sensor 11A according to the first embodiment. Therefore, like or corresponding portions are denoted with like reference numerals and the duplicated explanations are omitted.

The eddy current flaw detection sensor 11C of the present embodiment includes the two detection coils 2a, 2b different from each other in winding direction which are disposed between the two excitation coils 1a and 1b, and disposed in the axial direction of the retaining member 3. Signals can be detected which correspond to the positive and negative directions of bypass eddy currents D which flow in the circumferential direction while bypassing the circumferential crack E. Thus, the detection level of the signal is increased compared with the case of one detection coil, whereby the detection sensitivity of the circumferential crack E is enhanced and the occurrence position and size thereof can be precisely detected.

Fourth Embodiment of the Eddy Current Flaw Detection Sensor

Referring to FIG. 10, an eddy current flaw detection sensor 11D according to a fourth embodiment is characterized by disposing four detection coils 2a, 2b, 2c, 2d different from each other in winding direction between two excitation coils 1a, 1b so as to be arranged in a matrix manner. Among the four detection coils 2a, 2b, 2c, 2d, the detection coils 2a, 2d which are set in an oblique direction relative to the central axial direction S of the retaining direction 3 are the same in winding direction. The detection coils 2a, 2d and the other detection coils 2b, 2c are reversed to each other in winding direction. The detection coils 2b and 2c are the same in winding direction and are reverse in winding direction to the other coils 2a and 2d. The other portions are the same as those in the eddy current flaw detection sensor 11A according to the first embodiment. Therefore, like or corresponding portions are denoted with like reference numerals and the duplicated explanations are omitted.

The eddy current flaw detection sensor 11D of the present embodiment includes the four detection coils 2a, 2b, 2c, 2d different from each other in winding direction disposed between the two excitation coils 1a, 1b. Thus, the eddy current flaw detection sensor 11C of the present embodiment can further increase the detection level of the signal than the eddy current flaw detection sensor 11B of the second embodiment. The detection sensitivity of the circumferential crack E can be improved and the occurrence position and size thereof can be further precisely detected.

Fifth Embodiment of the Eddy Current Flaw Detection Sensor

Figure 11:
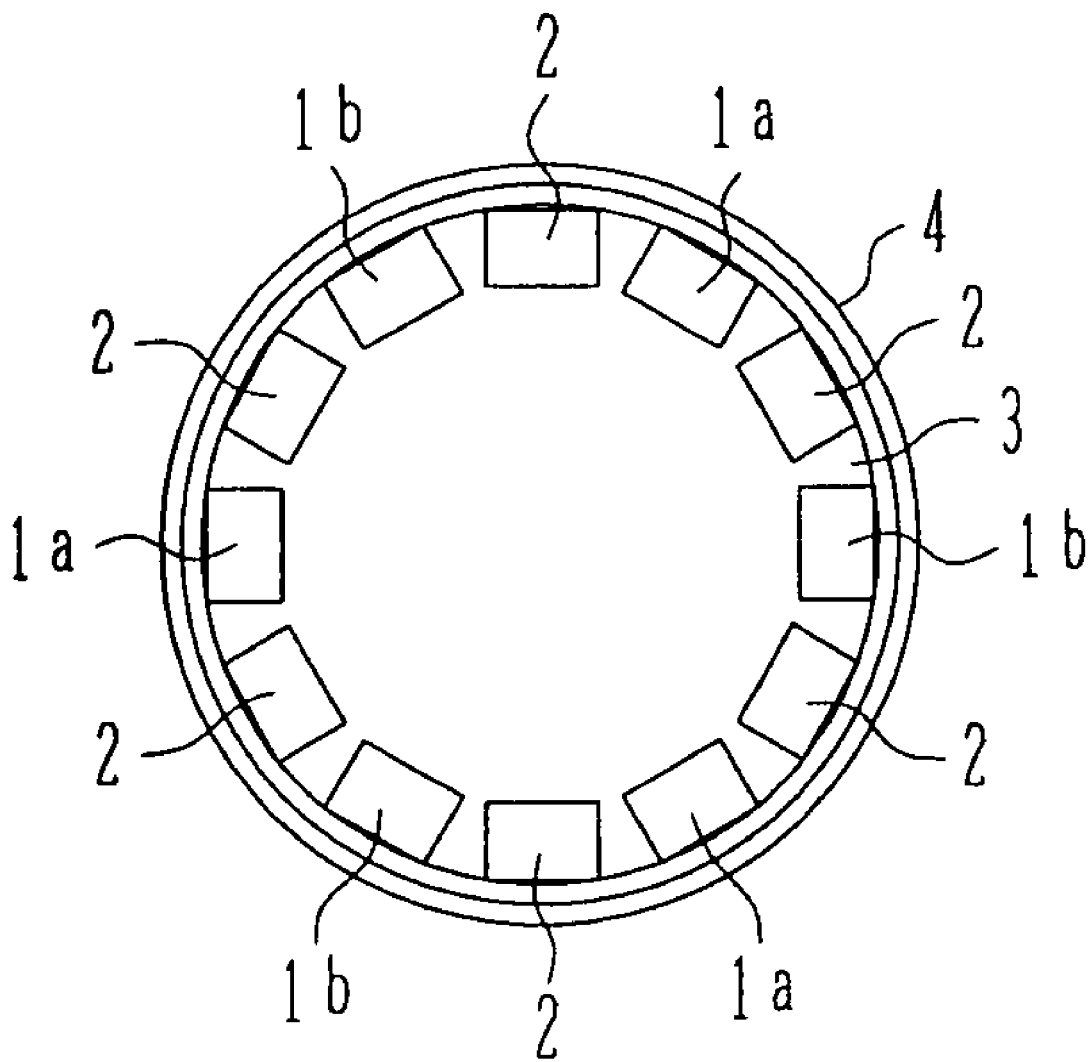
FIG. 11 is a view for assistance in explaining an eddy flaw detection sensor according to a fifth embodiment.
Figure 12A:
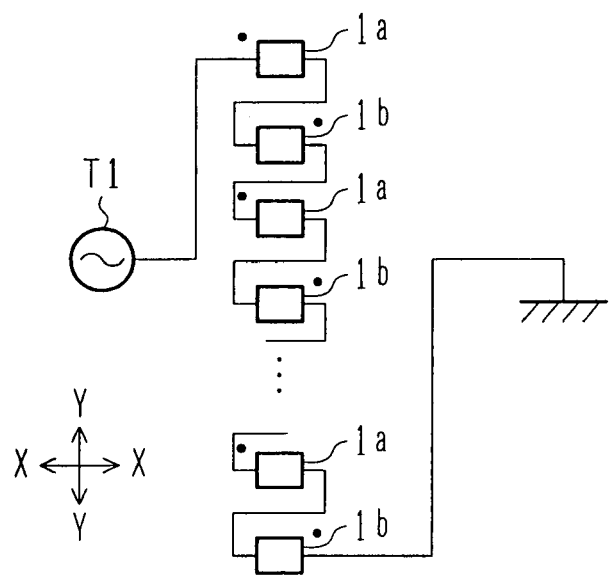
FIGS. 12A and 12B are connecting diagrams of the excitation coils for the eddy current flaw detection sensor according to the fifth embodiment.
Figure 12B:
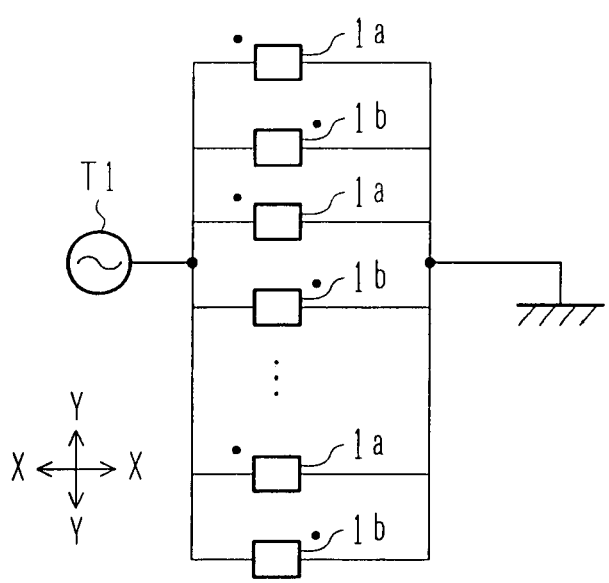

Referring to FIG. 11, an eddy current flaw detection sensor 11E of a fifth embodiment is characterized by being formed in a multi-channel manner in which a plurality of sets of coils are arranged on a retaining member 3 in the circumferential direction thereof, each set being constituted of two excitation coils 1a, 1b and at least one detection coil 2. The plurality of sets of excitation coils 1a, 1b arranged in the circumferential direction of the retaining member 3 are connected in series or parallel in such a manner that the winding directions of the adjacent excitation coils among the excitation coils arranged in the circumferential direction of the retaining member 3 through the detection coils 2 are reverse to each other as shown in FIGS. 12A and 12B. In addition, both ends of the wiring connection are connected to the input and output terminals of the multi-channel eddy current flaw detector 17 through lead wires. On the other hand, the detection coils 2 are connected to a desired detection circuit through the input and output terminals of the multi-channel eddy current flaw detector 17. The other portions are the same as those in the eddy current flaw detection sensor 11A according to the first embodiment. Therefore, like or corresponding portions are denoted with like reference numerals and the duplicated explanations are omitted. Incidentally, the 6-channel type eddy current flaw detection sensor equipped with six detection coils 2 is illustrated by way of example in the FIG. 11. However, the number of the channels is not limited to six and can be appropriately increased or decreased as necessary.

Figure 13:
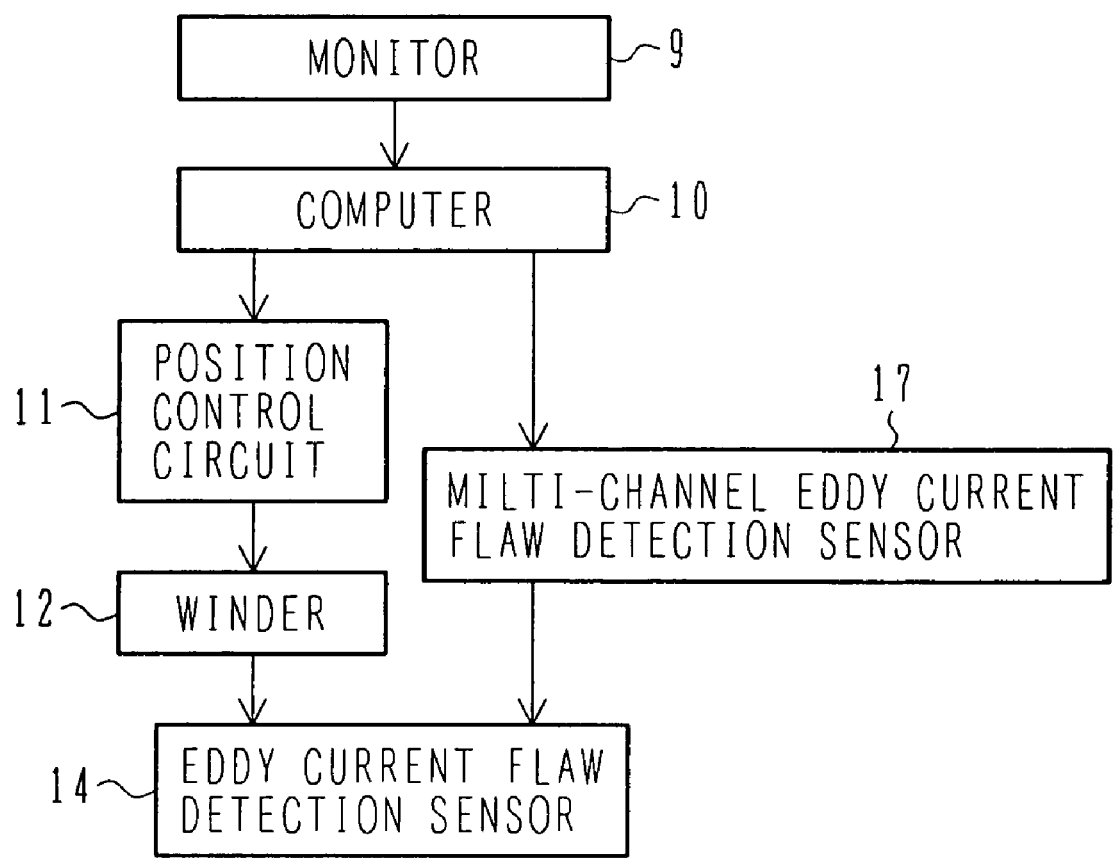
FIG. 13 is a block diagram illustrating the configuration of a multi-channel eddy current flaw detection system.

A description will be hereinafter made of a multi-channel eddy current flaw detection system using the eddy current flaw detector 11E of the fifth embodiment with reference to FIGS. 13 and 14. FIG. 13 is a block diagram of the multi-channel eddy current flaw detection system and FIG. 14 is a block diagram of the multi-channel eddy current flaw detector.

Referring to FIG. 13, the eddy current flaw detection system of the present embodiment includes an eddy current flaw detection sensor 11, a winder 12 for a lead wire connected to the eddy current flaw detection sensor 11, and a position control circuit 13 which controls an amount of feeding the lead wire from the winder 12. In addition, the eddy current flaw detection system includes the multi-channel eddy current flaw detector 17, a computer 15 and a monitor 16. The multi-channel eddy current flaw detector 17 feeds excitation current to the eddy current flaw detection sensor 11 and detects an induced voltage signal from the eddy current flaw detection sensor 11. The computer 15 controls drive of the winder 12 via the position control circuit 13 and drive of the eddy current flaw detection sensor 11 via the multi-channel eddy current detector 17. The monitor 16 displays the operating conditions of the above components, the induced voltage signal detected by the eddy current flaw detection sensor 11 and the like. The winder 12, the position control circuit 13, the eddy current flaw detector 14, the computer 15 and the monitor 16 may be commercially available ones.

Figure 14:
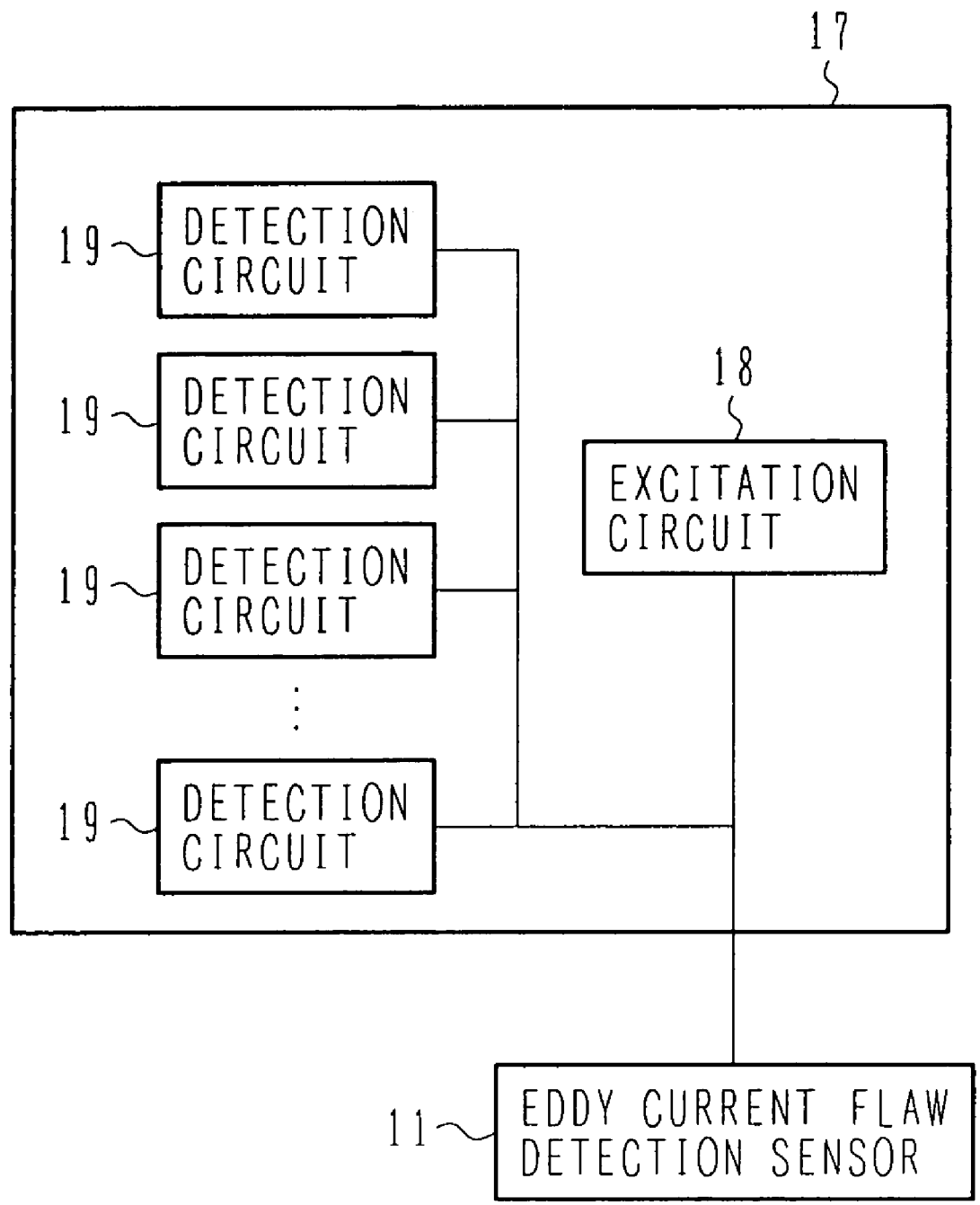
FIG. 14 is a block diagram illustrating the configuration of a multi-channel eddy current flaw detector.

Referring to FIG. 14, the multi-channel eddy current flaw detector 17 includes one excitation circuit 18 and detection circuits 19 whose number corresponds to the number of the channels of the eddy current detection sensor. The excitation circuit has a function of applying alternating voltage to the excitation coils provided for the eddy current flaw detection sensor. The detection circuit is configured to be able to output waveforms of a signal X and a signal Y based on the voltage obtained by each of the detection coils 2. The basic operational principles of the excitation circuit and the detection circuit in the multi-channel eddy current flaw detector 17 for outputting the waveforms of a signal X and a signal Y are the same as those of the eddy current flaw detector 14 shown in FIG. 2. The actual flaw detection using the multi-channel eddy current flaw detector 17 can obtain a signal X and a signal Y from a waveform output terminal associated with a corresponding one of the channels by connecting the eddy current flaw detection sensor 11E with the output and input terminals of the multi-channel eddy current flaw detector 17. Thus, the multi-channel eddy current flaw detection system including the eddy current detection sensor 11E and multi-channel eddy current flaw detector 17 of the present embodiment is used to parallel process the data of the channels according to the basic operational principles described with FIG. 2. Then, a signal X and a signal Y for each channel are output from a waveform output terminal associated with each channel. Incidentally, while the multi-channel eddy current flaw detector 17 has one excitation circuit by way of example, it is possible to install a plurality of the excitation circuits for meeting the same function as necessary.

A description will be hereinafter described of an experimental example of multi-channel eddy current flaw detection using the eddy current flaw detection sensor 11E and the multi-channel eddy current flaw detector 17 according to the fifth embodiment.

A simulated test object of the heat transfer tube that was used for the experiment had the same shape as the simulated test object shown in FIG. 5. In addition, the simulated test object was formed with a crack E which circumferentially extended in the outer surface thereof and had a depth of 1.15 mm. An eddy current flaw detection sensor 11E that was used for the experiment as the eddy current flaw detection sensor 11E was of a 8-channel type. The eddy current flaw detection sensor 11E according to the fifth embodiment was inserted into the simulated heat transfer tube 31 from the opening end thereof. Then, the eddy current flaw detection was performed on the simulated heat transfer tube 31 by appropriately changing the settings of the computer while monitoring the conditions with the monitor 16.

Figure 15A:
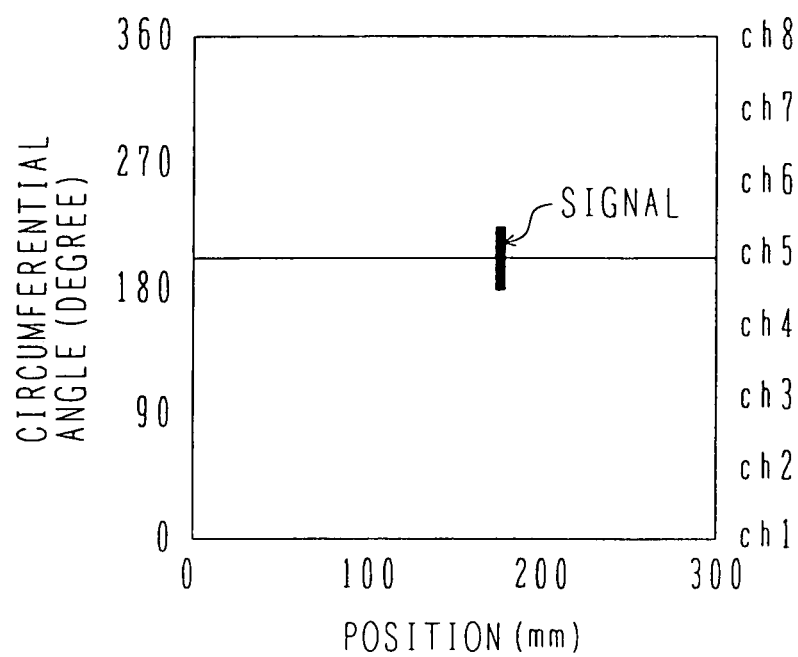
FIGS. 15A and 15B are waveform diagrams of a signal detected by a multi-channel eddy current flaw detection sensor.
Figure 15B:
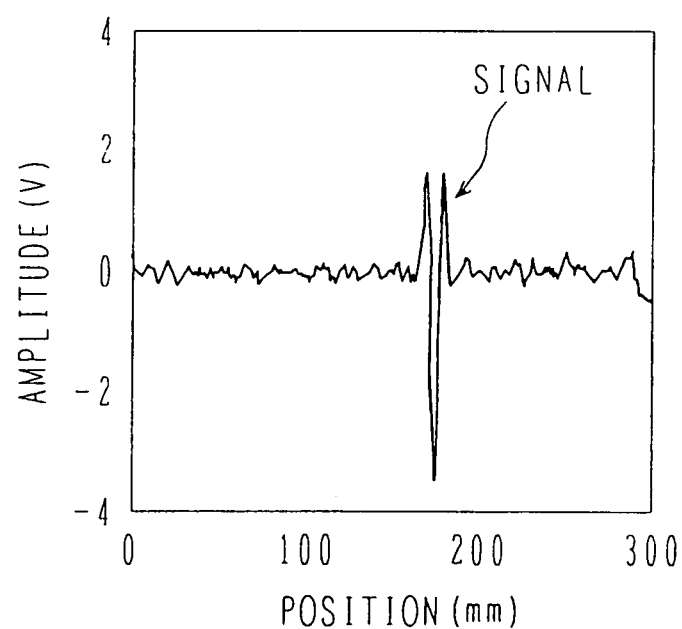

FIGS. 15A and 15B show a signal waveform obtained by the experimental example described above. As clearly from FIG. 15A, use of the eddy current flaw detection sensor 11E and the multi-channel eddy current flaw detector 17 according to the fifth embodiment can inspect the entire circumference of the simulated heat transfer tube 31 without omission. In addition, FIG. 5A shows that an external surface-circumferential crack E exists at the position of ch5. FIG. 5B shows a signal waveform resulting from the external surface-circumferential crack E detected at ch5. The experimental example confirms that the use of the eddy current flaw detection sensor 11E and the multi-channel eddy current flaw detector 17 according to the fifth embodiment can detect the external surface-circumferential crack E occurring at the tube expansion portion of the heat transfer tube. The eddy current flaw detection sensor 11E produces the same effects as those of the eddy current flaw detection sensor 11A, 11B, 11C and 11D according to the first, second, third and fourth embodiments, respectively. In addition to this, the eddy current flaw detection sensor 11E arranges the plurality of sets of coils on the retaining member 3 in the circumferential direction thereof, each set being constituted of two excitation coils 1a, 1b and at least one detection coil 2. Therefore, it is eliminated to operatively rotate the eddy current flaw detection sensor around the central axis of the heat transfer tube. In addition, a signal X and a signal Y obtained by a plurality of the detection coils 2 can be parallel processed and observed, thereby significantly streamlining the flaw inspection of the heat transfer tube.

Sixth Embodiment of the Eddy Current Flaw Detection Sensor

Figure 16A:
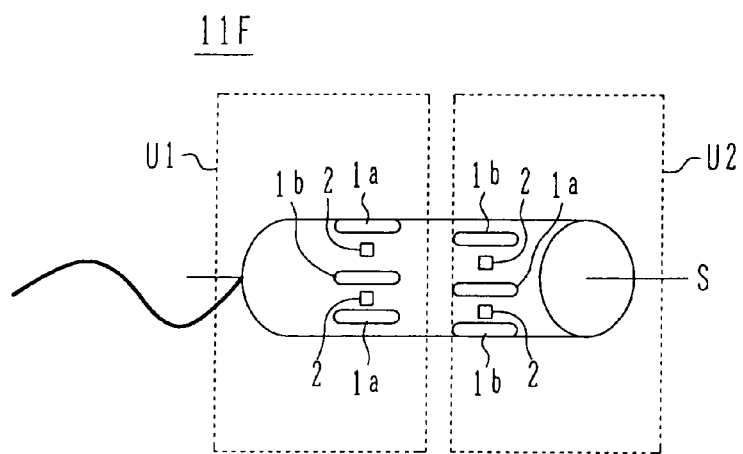
FIGS. 16A, 16B and 16C are diagrams for assistance in explaining an eddy current flaw detection sensor according to a sixth embodiment.
Figure 16B:
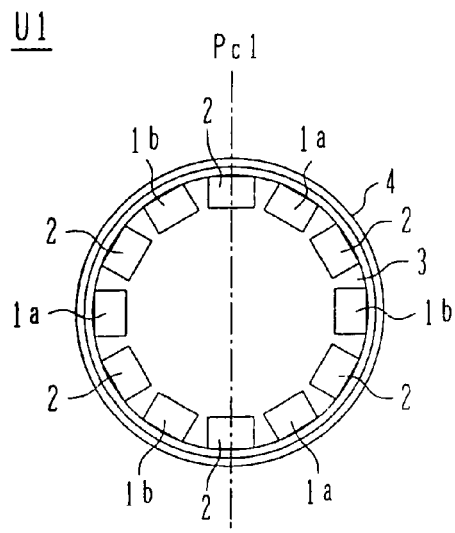
Figure 16C:
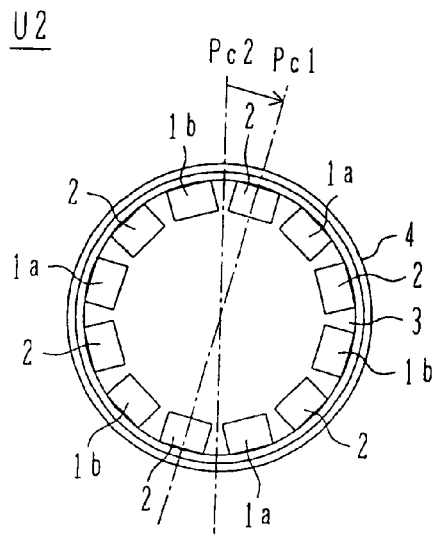
Figure 17A:
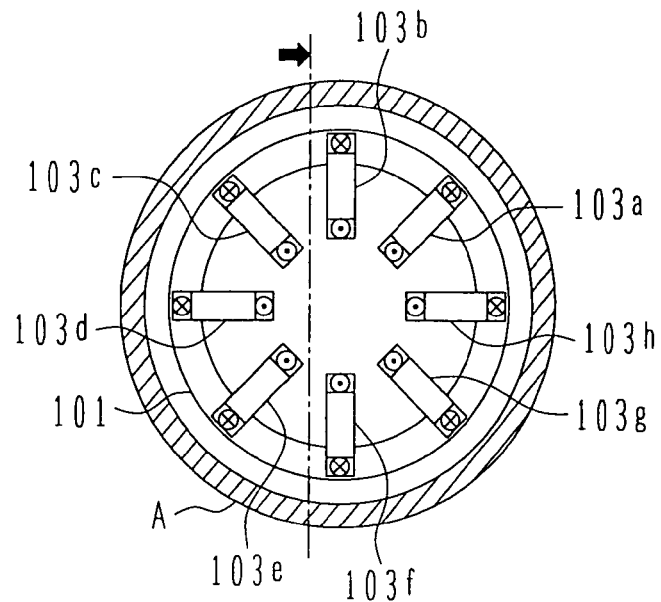
FIGS. 17A and 17B are cross-sectional views of a first example of a conventional eddy current flaw detection sensor.
Figure 17B:
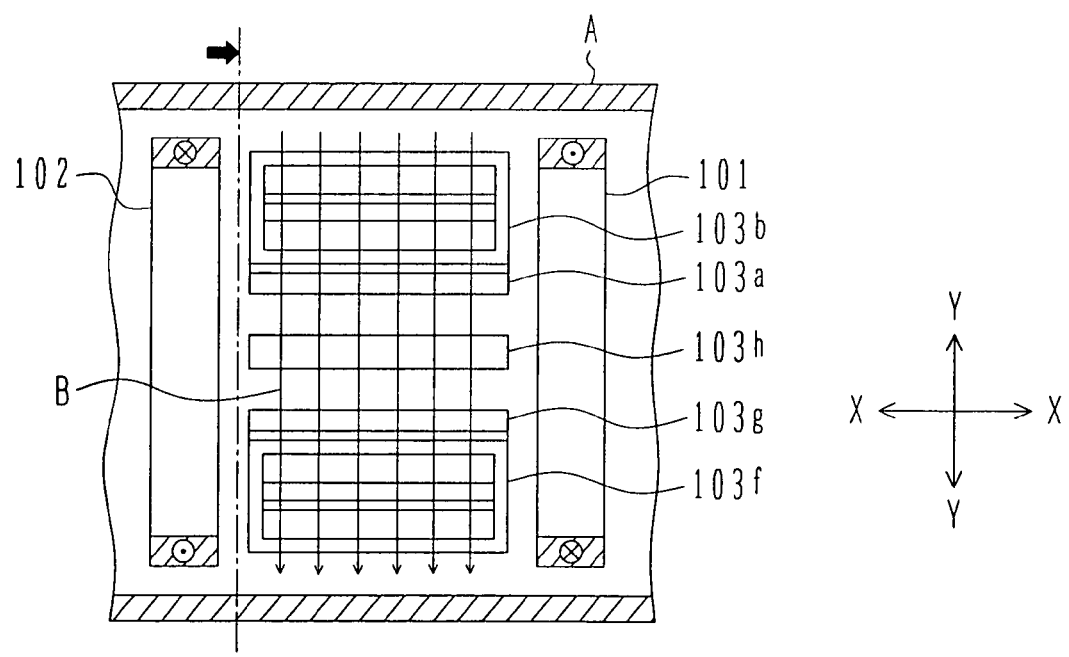
Figure 18:
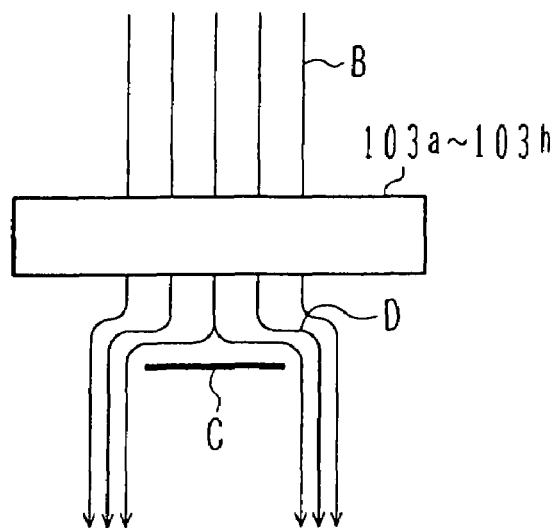
FIG. 18 is a diagram for assistance in explaining the operation of the conventional eddy current flaw detection sensor.
Figure 18:
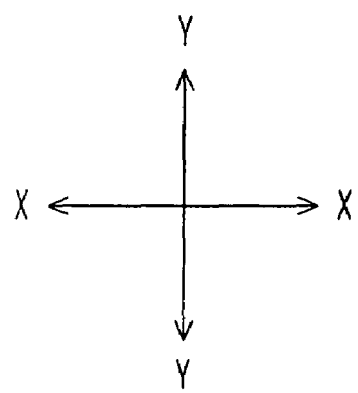
Figure 19A:
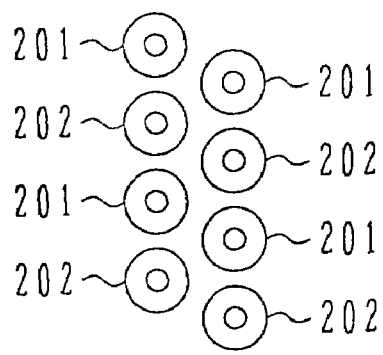
FIGS. 19A and 19B illustrate a second example of a conventional eddy current flaw detection sensor.
Figure 19B:
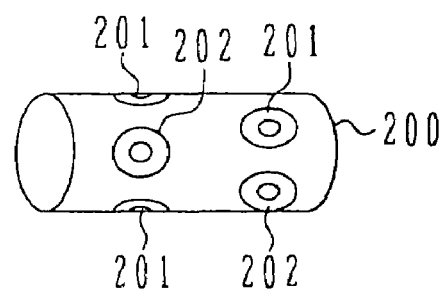
Figure 20:
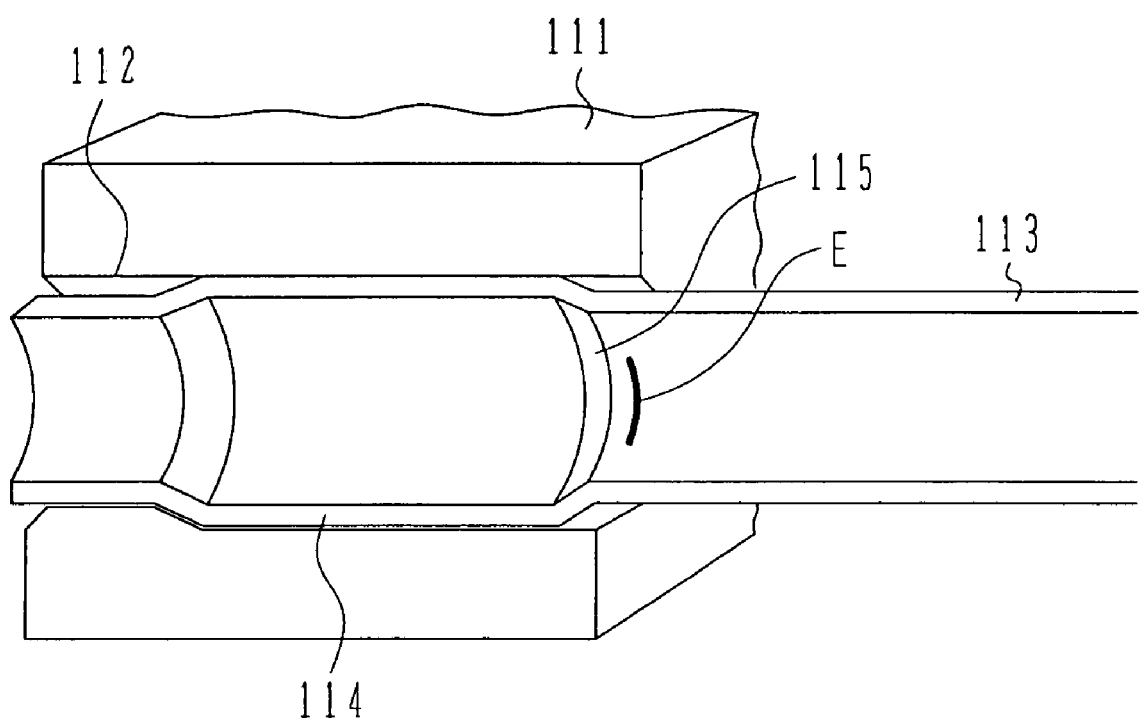
FIG. 20 is a cross-sectional view of an essential portion of a tube sheet and a heat transfer tube fastened to the tube sheet.
Figure 21:
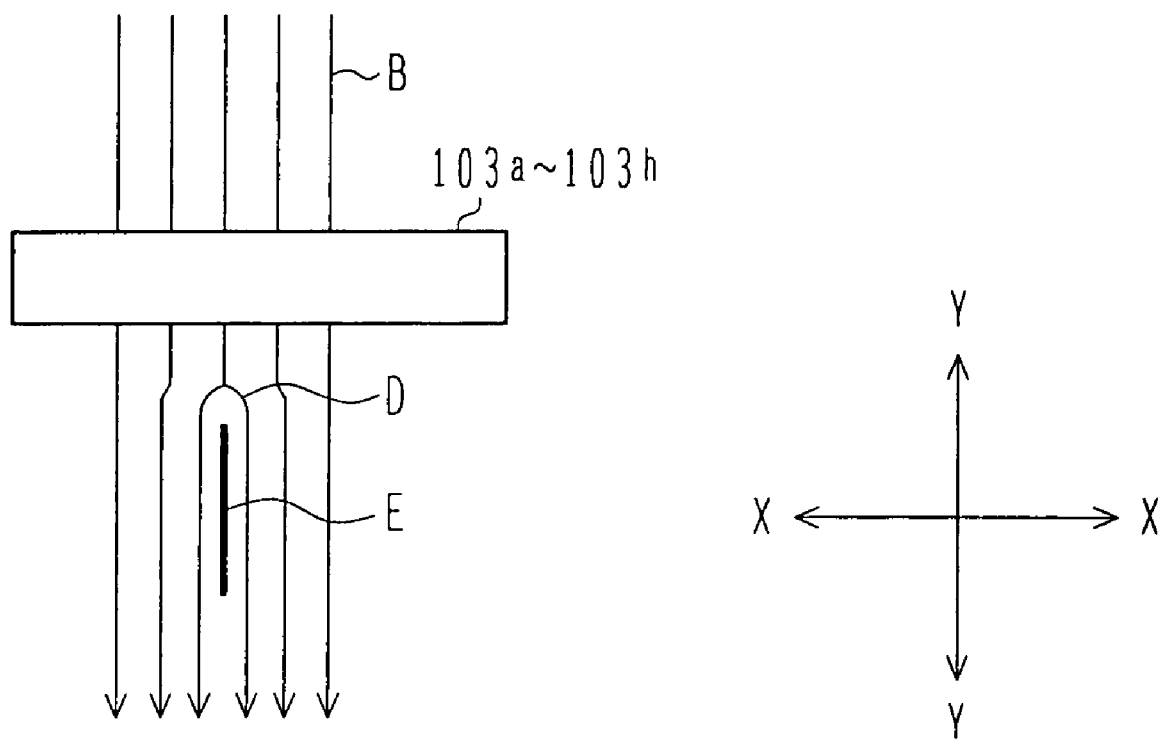
FIG. 21 is a diagram for assistance in explaining the disadvantage of the conventional eddy current flaw detection sensor.

Referring to FIGS. 16A, 16B and 16C, an eddy current flaw detection sensor 11F according to a sixth embodiment is characterized by the following: Sensor units U1, U2 are each composed of a plurality of sets of coils arranged in a retaining member 3 in the circumferential direction thereof, each set being constituted of two excitation coils 1a, 1b and at least one detection coil 2. A plurality of the sensor units U1, U2 are arranged so as to be spaced apart from each other in the axial direction of the retaining member 3. In addition, one set of the coils constituting one sensor unit U1 is offset from the other set of the coils constituting the other sensor unit U2 in the circumferential direction of the retaining member 3. In the sixth embodiment shown in FIGS. 16A, 16B and 16C, the set of the coils constituting the sensor unit U2 of a rear stage section is arranged to be offset from the set of the coils constituting the sensor unit U1 of a front stage section at a fifteen degrees in the circumferential direction of the retaining member 3. The other portions are the same as those in the eddy current flaw detection sensor 11E according to the fifth embodiment. Therefore, like or corresponding portions are denoted with like reference numerals and the duplicated explanations are omitted.

The eddy current flaw detection sensor 11F of the present embodiment is configured such that the set of the coils constituting one sensor unit U2 is arranged to be offset from the set of the coils constituting the other sensor unit U1 in the circumferential direction of the retaining member 3.

Thus, one of the sensor units can inspect the position, which corresponds to a dead zone for the other sensor unit, in the circumferential direction of the heat transfer tube, thereby making it possible to perform the inspection with a high degree of reliability.

What is claimed is:

1. An eddy current flaw detection sensor comprising:
   at least one detection coil; and
   excitation coils disposed on both sides of said detection coil;
   wherein a coil axis of said detection coil and coil axes of said excitation coils are arranged to intersect each other, and when said detection coil and said excitation coils are inserted into a tubular test object and excitation current is applied to said excitation coils, eddy current flows in the axial direction of the tubular test object and said detection coil can detect eddy current flowing in the circumferential direction of the tubular test body.

2. The eddy current flaw detection sensor according to claim 1, wherein a plurality of said excitation coils are evenly arranged in the circumferential direction of a retaining member and a single of or a plurality of said detection coils are evenly arranged between said excitation coils.

3. The eddy current flaw detection sensor according to claim 2, wherein two of said detection coils reverse to each other in winding direction are disposed between said excitation coils so as to be juxtaposed in an axial or circumferential direction of the retaining member.

4. The eddy current flaw detection sensor according to claim 2, wherein four of said detection coils reverse to each other in winding direction are disposed between said excitation coils so as to be arranged in axial and circumferential directions of the retaining member in a matrix manner.

5. The eddy current flaw detection sensor according to claim 1, wherein a winding wire of said excitation coil has a planar shape formed in an oval.

6. The eddy current flaw detection sensor according to claim 2, wherein the retaining member has an outer shape formed in a column.

7. The eddy current flaw detection sensor according to claim 2, comprising a plurality of sensor units arranged in an axial direction of the retaining member, each sensor unit including a plurality of excitation coils and a single of or a plurality of detection coils disposed between said excitation coils arranged in the circumferential direction of the retaining member;
   wherein said excitation coils and said detection coils constituting one of the sensor units are arranged to be offset from those constituting another of the sensor units in the circumferential direction of the retaining member.

8. The eddy current flaw detection sensor according to claim 7, wherein the plurality of excitation coils constituting the sensor units are connected in series or parallel in such a manner that the winding directions of two excitation coils disposed in the circumferential direction of the retaining member via said detector coil are alternately reversed with respect to a direction of applying excitation voltage, and both ends of the plurality of excitation coils connected in series or parallel are connected to one excitation power source.

9. An eddy current flaw detection method for detecting a flaw of a tubular test object by inserting, into the test object, an eddy current flaw detection sensor provided with an excitation coil and a detection coil,
   wherein said eddy current flaw detection sensor includes at least one detection coil and excitation coils disposed on both sides of the detection coil,
   a coil axis of the detection coil and coil axes of the excitation coils are arranged to intersect each other, and when the detection coil and the excitation coils are inserted into the tubular test object and excitation current is applied to the excitation coils, eddy current flows in the axial direction of the tubular test object and the detection coil can detect eddy current flowing in the circumferential direction of the tubular test body.

10. The eddy current flaw detection method according to claim 9, wherein said eddy current flaw detection sensor used is configured such that a plurality of the excitation coils are evenly arranged in the circumferential direction of a retaining member, a single of or a plurality of the detection coils are evenly arranged between the excitation coils and the plurality of excitation coils are connected in series or parallel, and
   wherein excitation voltage with the same waveform is applied to the plurality of excitation coils connected in series or parallel at the same time, thereby causing eddy currents reverse to each other in direction to flow under the detection coils adjacent to each other from the excitation coils arranged in the circumferential direction of the retaining member via the detection coil.

11. The eddy current flaw detection method according to claim 9, wherein the tubular test object is a tube expansion portion of a heat transfer tube of a heat exchanger provided for an atomic power plant.

12. The eddy current flaw detection method according to claim 10, wherein the tubular test object is a tube expansion portion of a heat transfer tube of a heat exchanger provided for an atomic power plant.

13. The eddy current flaw detection sensor according to claim 2, wherein a winding wire of said excitation coil has a planar shape formed in an oval.

14. The eddy current flaw detection sensor according to claim 3, wherein a winding wire of said excitation coil has a planar shape formed in an oval.

15. The eddy current flaw detection sensor according to claim 4, wherein a winding wire of said excitation coil has a planar shape formed in an oval.

* * * * *